United States Patent [19]

Pauling

[11] 3,981,896

[45] Sept. 21, 1976

[54] PHENYLSILOXY VANADIUM OXIDE CATALYSTS

[75] Inventor: Horst Pauling, Bottmingen, Switzerland

[73] Assignee: Hoffmann-La Roche Inc., Nutley, N.J.

[22] Filed: Feb. 21, 1975

[21] Appl. No.: 551,946

Related U.S. Application Data

[63] Continuation-in-part of Ser. No. 248,046, April 27, 1974, Pat. No. 3,919,250.

[30] Foreign Application Priority Data

Mar. 1, 1974   Switzerland.......................... 2932/74

[52] U.S. Cl. ........................ 260/429 R; 252/431 R
[51] Int. Cl.² .......................................... C07F 9/00
[58] Field of Search ................................ 260/429 R

[56]   References Cited
   UNITED STATES PATENTS

| | | | |
|---|---|---|---|
| 2,863,891 | 12/1958 | Granchelli et al. | 260/429 R |
| 2,994,711 | 8/1961 | Cohen | 260/429 R |
| 3,046,269 | 7/1962 | Cohen et al. | 252/431 R X |
| 3,324,195 | 6/1967 | Hwa et al. | 252/431 R X |
| 3,468,865 | 9/1969 | Santiago | 252/431 R X |
| 3,642,748 | 2/1972 | Iwasaki et al. | 252/431 R X |
| 3,920,751 | 11/1975 | Chabardes et al. | 260/601 R |

OTHER PUBLICATIONS

Chemical Abstracts, vol. 54, 4360c (1960).
Chemical Abstracts, vol. 58, 543g, 2508e (1963).
Chemical Abstracts, vol. 64, 12712d (1966).
Borisov et al., Organosilicon Heteropolymers and Heterocompounds, Plenum Press, N.Y. pp. 487–492 (1970).

*Primary Examiner*—Helen M. S. Sneed
*Attorney, Agent, or Firm*—Samuel L. Welt; Bernard S. Leon; William H. Epstein

[57]   ABSTRACT

Novel phenylsiloxy vanadium oxide catalyst where the phenyl moiety is substituted with an electron withdrawing group, said catalyst being used to convert secondary and tertiary acetylenic carbinols to the corresponding $\alpha,\beta$-unsubstituted carbonyl compounds.

12 Claims, No Drawings

PHENYLSILOXY VANADIUM OXIDE CATALYSTS

CROSS REFERENCE TO RELATED APPLICATIONS

This application is a continuation in part application of Ser. No. 248,046, Pauling filed Apr. 27, 1974 U.S. Pat. No. 3,919,250. Also related to this application is Ser. No. 410,930 filed Oct. 29, 1973 U.S. Pat. No. 3,912,656 — Andrews and Hindley.

BACKGROUND OF THE INVENTION

Certain α,β-mono-unsaturated aldehydes have heretofore been obtained by the catalytic rearrangement of corresponding tertiary acetylenic carbinols or derivatives thereof. For example, acetylenic carbinols have been converted to unsaturated aldehydes by a process involving initially esterifying the carbinols and then rearranging the ester derivative with the aid of a silver or copper catalyst. Typically, such rearrangement reactions have required several process steps, including the formation of an allene ester intermediate.

In an effort to reduce the number of process steps required for such catalytic rearrangement processes, catalysts derived from a metal of the Vth to VIIth sub-group of the periodic chart, particularly vanadium, niobium, molybdenum, tungsten and rhenium, have been utilized instead of copper or silver catalysts. Such catalysts have permitted acetylenic carbinols to be expeditiously rearranged to unsaturated aldehydes in a single operation.

However, the use of such catalysts of the Vth to VIIth sub-group has not been found to be completely satisfactory. Considerable loss of catalyst activity has been found to inevitably occur during the course of the rearrangement reaction. In addition, it has been discovered that decomposition products are formed during the rearrangement reaction as the catalyst loses activity and that these decomposition products cause the aldehyde product to be destroyed as it is formed, thereby reducing product yields.

SUMMARY OF THE INVENTION

In accordance with this invention it has been discovered that compounds of the formula:

wherein
$R_6$ is phenyl substituted, in one or more positions, with an electron withdrawing group; R is selected from the group consisting of alkyl, cycloalkyl, lower alkyl substituted cycloalkyl, phenyl, phenyl lower alkyl, lower alkyl substituted phenyl; lower alkyl substituted phenyl lower alkyl, —Si $(R_6)_3$ and Si $(R_5)_3$; $R_5$ is selected from the group consisting of alkyl, phenyl lower alkyl, cycloalkyl, lower alkyl-substituted cycloalkyl, phenyl; lower alkyl-substituted phenyl-lower alkyl, and lower alkyl substituted phenyl; m is an integer from 1 to 3; and n is an integer of from 0 to 2 with the proviso that the sum of m and n is 3.
are especially substituted as catalysts in the isomerization of a tertiary or a secondary acetylenic carbinol to α,β unsaturated aldehyde or ketone. By use of this catalyst, the isomerization of this invention can be carried out at low temperatures, i.e., from about room temperature to about 150°C. without the need for utilizing extreme elevated temperatures. This is extremely advantageous in the case where either the starting materials and end products are thermolabile.

The advantage obtained by utilizing the catalysts of formula III can be seen in the case of 3,7-dihydroxy-3,7-dimethyl-oct-1-yne and 2,5-dihydroxy-2,5-dimethyl-hex-3-yne, which largely decomposes at above 120°C and which cannot be isomerised with known catalysts which work predominantly in the range of this temperature. In accordance with this invention, these compounds can now be isomerized to 7-hydroxy-3,7-dimethyl-oct-2-en-1-al and 2-hydroxy-2,5-dimethyl-hex-4-en-3-one respectively is good yields using the novel catalysts of formula III at a temperature between room temperature and about 100°C.

DETAILED DESCRIPTION

The catalyst of formula III can be utilized to convert any secondary or tertiary acetylenic carbinol to the corresponding α,β unsaturated aldehyde or ketone. Among the preferred aldehydes and ketones produced by utilizing the catalyst of formula III are those having the following formula:

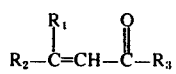

wherein
$R_1$ is hydrogen or lower alkyl, $R_2$ is alkyl, alkenyl, cycloalkenyl-substituted alkyl, cycloalkyl substituted alkyl, phenyl-alkyl, phenylalkenyl, phenyl, cycloalkyl, cycloalkenyl, cycloalkyl-substituted alkenyl, and cycloalkenyl-substituted alkenyl; $R_1$ and $R_2$ taken together with their attached carbon atom form a cycloalkyl or cycloalkenyl group; $R_3$ is hydrogen, alkyl, alkenyl, phenyl alkyl, phenyl alkenyl, cycloalkyl substituted alkenyl, cycloalkyl substituted alkyl, cycloalkenyl-substituted alkyl, cycloalkenyl substituted alkenyl, phenyl, cycloalkyl or cycloalkenyl and wherein said alkyl, alkenyl, cycloalkyl, cycloalkenyl and phenyl groups are unsubstituted or substituted in one or more positions with lower alkyl, lower alkoxy, hydroxy, lower alkanoyl, aroyl, lower alkanoyloxy or aroyloxy; and wherein said alkyl, alkenyl, cycloalkyl and cycloalkenyl groups can also be substituted with an additional substitutent selected from the group consisting of oxo or ketalised-oxo.

The process provided by the present invention comprises isomerising an alcohol of the general formula

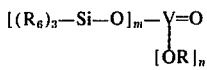

wherein
$R_1$, $R_2$ and $R_3$ are as above with the aid of a catalyst of formula III above.

The lower alkyl groups denoted by $R_1$ include both straight-chain and branched-chain hydrocarbon groups containing 1–6 carbon atoms such as methyl, ethyl, propyl, isopropyl and the like.

The alkyl groups which are denoted by $R_2$ and $R_3$ and which may be substituted can contain from 1 to 30 carbon atoms preferably from 1 to 20 carbon atoms and can be straight-chain or branched-chain.

The alkenyl groups denoted by $R_2$ and $R_3$ designated alkenyl groups containing from 2 to 30, preferably from 2 to 20 carbon atoms. The cycloalkenyl groups preferably containing from 3 to 7 carbon atoms such as cyclopropenyl, cyclopentenyl, cyclohexenyl etc.

Among the prefered catalysts of formula III are those catalysts where the phenyl group contains from 1 to 4, most preferably from 1 to 3, electron withdrawing substituents. Among the preferred catalysts are compounds of the formula

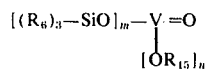   III-A wherein
$R_6$ is as above, $R_{15}$ is lower alkyl, cycloalkyl, phenyl, phenyl lower alkyl; lower alkyl phenyl, or —Si $(R_6)_3$ or —Si $(R_4)$; $R_4$ is lower alkyl, cycloalkyl, phenyl, phenyl lower alkyl, or lower alkyl phenyl and $m$ and $n$ are as above Particularly preferred is a compound of the formula

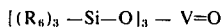

wherein
$R_6$ is as above

As examples of groups denoted by $R_2$ there may be mentioned the following: of the lower members preferably the methyl group and of the higher members which preferably have an isoprene or isoprene-like structure the
 4-methyl-pent-3-enyl;
 4,8-dimethyl-nona-3,7-dienyl;
 4,8,12-trimethyl-tridecyl;
 4-hydroxy-4-methyl-pentyl; and
 4-methoxy-4-methyl-pentyl groups.

Examples of groups denoted by $R_3$ are: of the lower members the propyl group and of the higher members the
 2,6-dimethyl-hepta-1,3,5-trienyl group.

The aforementioned optionally substituted cycloalkyl component of the group $R_2$ can contain from 1 to 20 carbon atoms. Examples of such cycloalkyl groups linked with a straight-chain or branched-chain alkyl or alkenyl group $R_2$, preferably one having an isoprene or isoprene-like structure, are the
 2-(2,6,6-trimethyl-cyclohex-1-en-1-yl)-vinyl;
 2-(4-oxo-2,6,6-trimethyl-cyclohex-1-en-1-yl)-vinyl;
 2-(4-ethylenedioxy-2,6,6-trimethyl-cyclohex-1-en-1-yl)-vinyl;
 6-(2,6,6-trimethyl-cyclohex-1-en-1-yl)-4-methyl-hexa-1,3,5-trienyl;
 6-(4-oxo-2,6,6-trimethyl-cyclohex-1-en-1-yl)-4-methyl-hexa-1,3,5-trienyl; and
 6-(4-ethylenedioxy-2,6,6-trimethyl-cyclohex-1-en-1-yl)-4-methyl-hexa-1,3,5-trienyl groups.

Examples of alcohol starting materials of formula II hereinbefore in which $R_1$ and $R_2$ are joined together to form a cycloalkyl or cycloalkenyl group are:
 1-ethynyl-cyclohexanol;
 4-ethynyl-4-hydroxy-1-oxo-3,5,5-trimethyl-cyclohex-2-ene; and
 4-ethynyl-4-hydroxy-1-ethylenedioxy-3,5,5-trimethyl-cyclohex-2-ene.

The substituents which may be present on the aforementioned alkyl, alkenyl, cycloalkyl, cycloalkenyl and phenyl groups are lower alkyl groups containing 1–6 carbon atoms (e.g. methyl, ethyl, propyl, isopropyl and the like), lower alkoxy groups containing 1–6 carbon atoms (e.g. methoxy, ethoxy, propoxy, isopropoxy and the like), lower alkanoyl groups containing 1–6 carbon atoms (e.g. formyl, acetyl, propionyl, butyryl and the like), aroyl groups (especially the benzoyl group), lower alkanoyloxy groups containing 2–6, preferably 2 to 6, carbon atoms (e.g. acetoxy, propionyloxy, butyryloxy and the like) and aroyloxy groups (especially the benzoyloxy group). The alkyl, alkenyl, cycloalkyl and cycloalkenyl groups may also be substituted by oxo or by ketalised-oxo. An oxo group can be ketalised with a lower alkanol (e.g. methanol) or glycol (e.g. ethyleneglycol).

In the compound of formula III, R is preferably a lower alkyl, phenyl, lower alkyl-phenyl or phenyl(lower alkyl) group, the two latter groups containing from 1 to 10 carbon atoms. Examples for lower alkyl groups are methyl, ethyl, isopropyl or n-butyl. Examples for lower alkyl-substituted phenyl groups are tolyl or xylyl. Examples for phenyl-(lower alkyl) groups are benzyl or phenethyl.

Of the oxo compounds of formula I hereinbefore, the following four groups represented by formulae IA, IB, IC and ID are especially important:

   (IA)

wherein
R'$_1$ and R'$_2$ taken together form a cycloalkyl or cycloalkenyl group which may be unsubstituted or substituted with lower alkyl, lower alkoxy, hydroxy, oxo or ketalized-oxo;

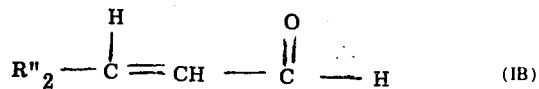   (IB)

wherein
R''$_2$ is cycloalkyl, cycloalkenyl or phenyl which may be unsubstituted or substituted with lower alkyl, lower alkoxy, hydroxy or, except in the case of phenyl, by oxo or ketalized-oxo;

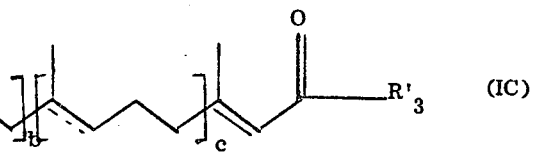   (IC)

wherein
R'$_3$ is hydrogen or lower alkyl and $a=1$, $b=1$ and $c=1$, or $a=0$, $b=1$ and $c=1$, or $a=0$, $b=0$ and $c=1$, or $a=0$ $b=0$ and $c=0$ and the broken lines can be hydrogenated or can denote optional carbon-carbon bonds and wherein hydroxy or lower alkoxy substituents may be substituted on the carbon atoms in the groupings a, b and/or c;

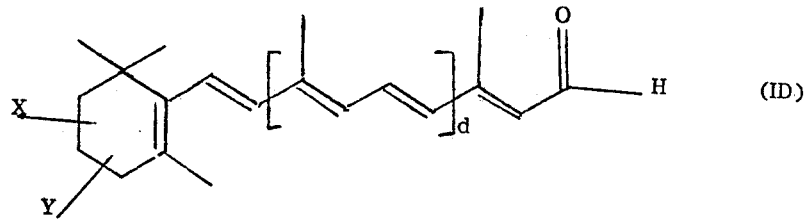

wherein
X is hydrogen or hydroxy and Y is oxo or hydrogen.

The alcohols of formula II required as starting materials for the manufacture of the oxo compounds of formulae IA, IB, IC, and ID hereinbefore have the following general formulae

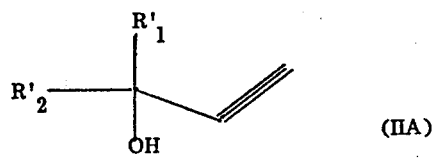

wherein
R'$_1$ and R'$_2$ are as above

wherein
R''$_2$ are as above;

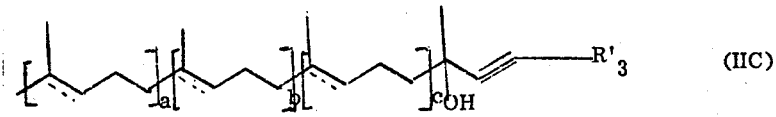

wherein
R'$_3$, a, b and c and the broken lines are as above and hydroxy or lower alkoxy substituents may be substituted on the carbon atoms within the groupings a, b and/or c;

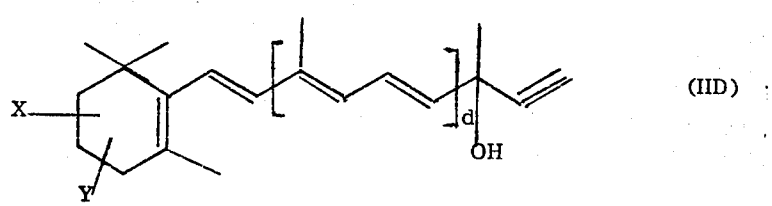

wherein
X and Y are as above.

The process provided by the present invention has proved to be particularly favorable and advantageous for the manufacture of the following oxo compounds:
cyclohexylidene-acetaldehyde;
(4,4-ethylenedioxy-2,6,6-trimethyl-cyclohex-2-en-1-ylidene)-acetaldehyde;
cinnamaldehyde;
2-methyl-hept-2-en-4-one;
senecioaldehyde;
citral;
7-hydroxy-citral; [7-hydroxy-3,7-dimethyl-oct-2-en-1-al]
7-methoxy-citral; [7-methoxy-3,7-dimethyl-oct-2-en-1-al]
farnesal;
phytal;
β-C$_{15}$-aldehyde [5-(2,6,6-trimethyl-cyclohex-1-en-1-yl)-3-methyl-penta-2,4-dien-1-al]
vitamin A aldehyde.

The phenyl group denoted by R$_6$ in the catalysts of formula III must carry one or more electron-withdrawing substituents.

Included among the electron-withdrawing substitutents are particularly those listed in "Textbook of Organic Chemistry", Fieser and Fieser, 1954 Ed., page 651, namely:
NO$_2$,
CN,
COCH$_3$,
CHO,
COOC$_2$H$_5$,
Cl,
Br,
I
and COOH,
as well as
F,
CF$_3$
and
C$_6$H$_5$.

Examples of catalysts of formula III hereinbefore are:
- tris-[tri-(p-fluorophenyl)-siloxy]vanadium oxide,
- tris-[tri-(p-chlorophenyl)-siloxy]vanadium oxide,
- tris-[tri-(p-bromophenyl)-siloxy]-vanadium oxide,
- tris-[tri-($\alpha,\alpha,\alpha$,-trifluoro-m-tolyl)-siloxy]-vanadium oxide,
- tris-[bis-(3-nitro-4-bromophenyl)-(4-bromophenyl)-silox]-vanadium oxide,
- (tri-p-flourophenyl)-siloxy-bis-(triphenyl-siloxy)-vanadium oxide,
- tri-[tri-(4-biphenylyl)-siloxy]-vanadium oxide,
- bis-[tri-(p-fluorophenyl)-siloxy]-triphenyl-siloxy-vanadium oxide, and
- bis-[tri-(p-bromophenyl)-siloxy]-cyclohexyloxy-vanadium oxide.

The catalysts of formula III hereinbefore are novel and it will be appreciated that they also form part of the present invention. They can be prepared according to methods known per se; for example, by i. the reaction of vanadium pentoxide with a silanol of the formula (R$_6$)$_3$ SiOH (wherein R$_6$ is a phenyl group which is substituted by one or more electron-withdrawing substituents) with azeotropic removal of the water formed in the reaction with the aid of a water-entraining agent such as, for example, benzene;

ii. the reaction of vanadium oxytrichloride with a silanol of the formula (R$_6$)$_3$SiOH (wherein R$_6$ is a phenyl group which is substituted by one or more electron-withdrawing substituents) in the presence of a base such as, for example, pyridine or ammonia;

iii. the reaction of a vanadium acid ester of the formula [R']$_3$—V=O (wherein R' is a lower alkoxy group) with a silanol of the formula (R$_6$)$_3$SiOH (wherein R$_6$ is a phenyl group which is substituted by one or more electron-withdrawing substituents), if necessary in the presence of catalytic amounts of an alkyl- or phenyl-alkali silanolate (e.g. a trialkyl alkali silanolate):

iv. the reaction of a siloxy-vanadium oxide of the formula [(R'')$_3$SiO]$_3$—V=O (wherein R'' represents a lower alkyl group) with a silanol of a formula (R$_6$)$_3$SiOH (wherein R$_6$ is a phenyl group which is substituted by one or more electron-withdrawing substituents), if necessary in the presence of catalytic amounts of an alkali silanolate such as a tri(lower alkyl)-alkali silanolate:

v. the reaction of vanadium oxytrichloride with an alkali silanolate of the formula (R$_6$)$_3$SiOMe(I) (wherein R$_6$ is a phenyl group which is substituted by one or more electron-withdrawing groups and Me is a alkali metal) in an inert solvent such as diethyl ether;

vi. the reaction of silver orthovanadate of the formula Ag$_3$VO$_4$ with a silyl halide of the formula (R$_6$)$_3$—Si-Hal (wherein R$_6$ is a phenyl group which is substituted by one or more electron withdrawing substituents and Hal represents a halogen atom) in a solvent such as benzene or methylene chloride;

vii. the double reaction of a vanadium acid ester of the formula [R']$_3$—V=O (wherein R' is a lower alkoxy group) with a silyl ester of the formula (R$_6$)$_3$—Si—O—COR'' (wherein R$_6$ represents a phenyl group which is substituted by one or more electron-withdrawing substituents and R'' represents a lower alkyl group), for example of tripropyl orthovanadate with triphenyl silyl acetate with the liberation of propyl acetate, conveniently in a solvent (e.g. n-heptane) in which the resulting ester forms an azeotrope which is separable from the reaction mixture.

The catalytic isomerisation of acetylenic carbinols of formula II to $\alpha,\beta$-unsaturated oxo compounds of formula I in accordance with the present invention is conveniently carried out by heating a corresponding carbinol together with the catalyst for some time, expediently in the presence of an inert solvent. The catalytic isomerisation is expediently carried out using about 0.1 to about 5 mol %, preferably about 1.5 to about 2 mol %, of catalyst of formula III based on the substrate, i.e., the compound of formula II. The catalytic can be carried out in the presence of, or with the exclusion of, air.

This reaction can be carried out in the presence of an inert organic solvent. Any conventional inert organic solvent can be utilized. Among the suitable solvents are, for example, aliphatic hydrocarbons (e.g. heptane, cyclohexane, cyclododecane, decalin, paraffin and paraffin oil), aromatic hydrocarbons (e.g. benzene, nitrobenzene, toluene and xylene), halogenated hydrocarbons (e.g. chlorobenzene), ethers (e.g. anisole and dioxane) and amines (e.g. N-methylaniline). Polymeric silicon-containing solvents such as silicon oils containing aliphatic or aromatic groups (e.g. methyl-phenyl-polysiloxane) can also be used.

The temperature at which the present catalytic isomerisation is carried out can vary from room temperature (20°C) to about 150°C. It is expedient to carry out the catalytic isomerisation at a temperature of from about 40°C to 110°C.

If necessary, the catalytic isomerisation can also be carried out under pressure, in which case pressures up to about 50 atmospheres can be used. However, this reaction can be carried out at atmospheric pressure. However, for best results as far as yields are concerned times of reaction of from about 2 to 20 hours are generally utilized. Reaction times of greater than 20 hours can be utilized if desired. However, no additional beneficial results are achieved from utilizing long reaction times.

The catalyst used in the present catalytic isomerisation retains practically its complete activity during the isomerisation. It can accordingly be used for carrying out many isomerisation batches before it requires replacement.

The isomerisation product is separated from the unreacted portions of the alcohol starting material in the usual manner; for example, by rectification. The unreacted carbinol portions can again be used in the subsequent batch. By following this procedure there are generally obtained conversions of 70% to 80% by weight and, depending on the alcohol starting material used, yields of greater than 90% by weight.

The following Examples are illustrative but not limitative of the present invention:

EXAMPLE 1

Preparation of
tris-[tri-(p-fluorophenyl)-siloxy]-vanadium oxide 1 g of tri-(p-fluorophenyl)-silanol are dissolved in 30 ml of absolute benzene. The solution is treated, with the exclusion of moisture, with 0.255 ml of pyridine and 0.173 g of vanadium oxytrichloride. The mixture obtained is stirred for 8 hours at room temperature and then heated to boiling for 2 hours under reflux. The pyridine hydrochloride which separates after cooling to 10°C is filtered off. The filtrate is evaporated under reduced pressure. The residual tris-[tri-(p-fluorophenyl)-siloxy]-vanadium oxide melts at 147°C after recrystallization from n-heptane.

EXAMPLE 2

By the procedure of Example 1:
vanadium oxytrichloride is reacted with tri-(p-chlorophenyl)-silanol [m.p. 127°–128°C] to produce tris-[tri-(p-chlorophenyl)-siloxy]vanadium oxide [m.p. 181°C.]; vanadium oxytrichloride is reacted with tri-(p-bromophenyl)-silanol [m.p. 120°–121°C.] to produce the tris-[tri-(p-bromophenyl)-silox]-vanadium oxide [m.p. 175°C.]; and vanadium oxytrichloride is reacted with tri-4-biphenylyl-silanol [m.p. 199°–200°C.] to produce tris-[tri-(4-biphenylyl)-siloxy]-vanadium oxide.

EXAMPLE 3

Preparation of
tris-[tri-$\alpha,\alpha,\alpha$-trifluoro-m-tolyl)-siloxy]-vanadium oxide.

0.5 g of tri-($\alpha,\alpha,\alpha$, trifluoro-m-tolyl)-silanol [m.p. 72°–73°C.] are dissolved in 30 ml of absolute benzene. The resulting solution is treated with 0.115 g of tris-(trimethyl-siloxy)-vanadium oxide. The mixture is heated to boiling under reflux for 1 hour. 20 ml of benzene together with the resulting trimethyl silanol are first distilled off from the mixture at normal pressure and subsequently, after the addition of 20 ml of toluene, a further 20 ml of a benzene/toluene mixture are distilled off at normal pressure. The toluene solution is evaporated at 50°C under reduced pressure. There is obtained tris-[tri-($\alpha,\alpha,\alpha$,-trifluoro-m-tolyl)-siloxy]-vanadium oxide [mol peak = 1504].

EXAMPLE 4

By the procedure of Example 3:
tris-(trimethylsiloxy)-vanadium oxide is reacted with tris ($\alpha,\alpha,\alpha$,-trifluoro-p-tolyl)-silanol to produce tri-[tri-($\alpha,\alpha,\alpha$,-trifluoro-p-tolyl)-siloxy]-vanadium oxide [mol peak = 1504];
tris-(trimethylsiloxy)-vanadium oxide is reacted with tri-(p-fluorophenyl)-silanol and triphenylsilanol in a molar ratio of 1:1:2 to produce (tri-p-fluorophenyl)-siloxy-bis-(triphenylsiloxy)-vanadium oxide [m.p. 203°C];
tris-(trimethylsiloxy)-vanadium oxide is reacted with tri-(p-fluorophenyl)-silanol and triphenylsilanol in a molar ratio of 1:2:1 to produce bis-[tri-(p-fluorophenyl)-siloxy]-triphenylsiloxy-vanadium oxide [mol peak = 1000];
tris-(trimethylsiloxy)-vanadium oxide is reacted with tri-(p-bromophenyl)-silanol and cyclohexanol in a molar ratio of 1:2:1 to produce bis-[tri-p-bromophenyl)-siloxy]-cyclohexyloxy-vanadium oxide [mol peak = 1184 ref to $^{79}$Br]; and
tris-(trimethylsiloxy)-vanadium oxide is reacted with bis-(3-nitro-4-bromophenyl)-(4-bromophenyl)-silanol to produce tris-[bis-(3-nitro-4-bromophenyl)-(4-bromophenyl)-siloxy]-vanadium oxide [mol peak = 1873 ref. to $^{79}$Br].

EXAMPLE 5

1 g of tri-(p-bromophenyl)-silanol is dissolved in 10 ml of sulpholane. The solution obtained is treated dropwise, with the exclusion of moisture and at 10°C, with 0.98 g of nitronium tetrafluoroborate [$NO_2BF_4$] in 25 ml of sulpholane. The mixture is stirred at room temperature for 1 hour, then introduced into a sodium hydrogen carbonate solution and extracted with diethyl ether. The ether extract is washed with a saturated aqueous sodium sulphate solution, dried over sodium sulphate and evaporated under reduced pressure at room temperature. The residual bis-(3-nitro-4-bromophenyl)-(4-bromophenyl)-silanol melts at 211°C after recrystallization from nitrobenzene/petroleum ether.

EXAMPLE 6

A mixture of 0.835 g of 3-hydroxy-3,7-dimethyl-oct-6-en-1-yne [dehydrolinalool], 8.885 ml. of high-boiling paraffin oil [b.p. 120°C/0.1 mm Hg] and 0.105 g of tris-[tri-(p-fluoro-phenyl)-siloxy]-vanadium oxide is stirred for 8 hours at 95°C with the exclusion of moisture. The resulting citral is separated from unreacted dehydrolinallol by rectification. The conversion of dehydrolinalool employed amounts to 0.69 g corresponding to 83% by weight. The yield of citral base on reacted dehydrolinalool amounts to 0.56 g corresponding to 81% by weight.

EXAMPLE 7

By the procedure of Example 6, 3,7-dihydroxy-3,7-dimethyl-oct-1-yne is isomerised in the presence of tris-[tri-($\alpha,\alpha,\alpha$-trifluoro-m-tolyl)-siloxy]-vanadium oxide over a period of 6 hours at 95°C to give 7-hydroxy-3,7-dimethyl-oct-2-en-1-al[7-hydroxy-citral]. The conversion of 3,7-dihydroxy-3,7-dimethyl-oct-1-yne amounts to 84%. The yield of 7-hydroxy-citral based on the reacted acetylenic carbinol amounts to 86% by weight.

EXAMPLE 8

By procedure of Example 6 2,5-dihydroxy-2,5-dimethyl-hex-3-yne is isomerised in the presence of tris-[tri-($\alpha,\alpha,\alpha$-trifluoro-p-tolyl)-siloxy]-vanadium oxide over a period of 7 hours at 105°C to give 2-hydroxy-2,5-dimethyl-hex-4-en-3-one. The conversion of 2,5-dihydroxy-2,5-dimethyl-hex-3-yne amounts to 84% by weight. The yield of 2-hydroxy-2,5-dimethyl-hex-4-en-3-one based on the reacted acetylenic carbinol amounts to 87.5% by weight.

EXAMPLE 9

The isomerisation of dehydrolinalool to citral described in Example 6 was carried out with the catalysts listed hereinafter under the conditions given in Example 6. The following results were obtained, with the percent conversion and percent yield given in by weight percent.

| | |
|---|---|
| Catalyst: | tris-[tri-(p-chlorophenyl)-siloxy]-vanadium oxide |
| Conversion of: | dehydrolinalool = 78% |
| Yield of: | citral = 86%; |
| Catalyst: | tris-[tri-(p-bromophenyl)-siloxy]-vanadium oxide |
| Conversion of: | dehydrolinalool = 81% |
| Yield of: | citral = 88%; |
| Catalyst: | tris-[tri-(4-biphenylyl)-siloxy]-vanadium oxide |
| Conversion of: | dehydrolinalool = 73% |
| Yield of: | citral = 79%; |
| Catalyst: | (tri-p-fluorophenyl)-siloxy-bis-(triphenylsiloxy)-vanadium oxide |
| Conversion of: | dehydrolinalool = 62% |
| Yield of: | citral = 71%; |
| Catalyst: | bis-[tri-(p-fluorophenyl)-siloxy]-triphenylsiloxy-vanadium oxide |
| Conversion of: | dehydrolinalool = 68% |
| Yield of: | citral =74%; |
| Catalyst: | bis-[tri-(p-bromophenyl)-siloxy]-cyclohexyloxy-vanadium oxide |
| Conversion of: | dehydrolinalool = 66% |
| Yield of: | citral = 79%; and |
| Catalyst: | tris-[bis-3-nitro-4-bromophenyl)-4-bromophenyl)-siloxy]-vanadium oxide |
| Conversion of: | dehydrolinalool = 59% |
| Yield of: | citral = 71%. |

EXAMPLE 10

8.4 g. of 3-hydroxy-3-methyl-but-1-yne, 1 g. of tris-[tri-($\alpha,\alpha,\alpha$-trifluoro-m-tolyl)-siloxy]-vanadium oxide and 50 ml of high-boiling paraffin oil ($D_{20}^4 = 0.885$) are stirred at 90°C. for 15 hours with the exclusion of moisture. The conversion of acetylenic carbinol used amounts to 6.3 g. corresponding to 75% by weight. The yield of 3-methyl-but-2-en-1-al amounts to 5.2 g. corresponding to 82.5% by weight.

EXAMPLE 11

22 g. of 3-hydroxy-3,7,11-trimethyl-dodeca-6,10-dien-1-yne, 0.7 g. of tris-[tri-($\alpha,\alpha,\alpha$-trifluoro-p-tolyl)-siloxy]-vanadium oxide and 200 ml of silicon oil are heated to 105°C. for 5 hours with the exclusion of moisture. The conversion of the acetylenic carbinol used amounts to 15.9 g. corresponding to 72% by weight. The yield of 3,7,11-trimethyl-dodeca-2,6,10-trien-1-al amounts to 13.0 g. corresponding to 82% by weight.

EXAMPLE 12

29.4 g. of 3-hydroxy-3,7,11,15-tetramethyl-hexadec-1-yne, 0.75 g. of tris-[tri-($\alpha,\alpha,\alpha$-trifluoro-m-tolyl)-siloxy]-vanadium oxide and 500 ml. of high-boiling paraffin oil are heated to 100°C. for 6 hours with the exclusion of moisture. The conversion of the acetylenic carbinol used amounts to 14.4 g. corresponding to 49% by weight. The yield of 3,7,11,15-tetramethyl-hexadec-2-en-1-al amounts to 11.1 g. corresponding to 77.2% by weight.

EXAMPLE 13

18.4 g. of 3-hydroxy-7-methoxy-3,7-dimethyl-oct-1-yne [7-methoxydehydrolinalool], 0.7 g. of tris-[tri-($\alpha,\alpha,\alpha$-trifluoro-p-tolyl)-vanadium oxide] and 150 ml of high-boiling paraffin oil are stirred for 8 hours at 95°C. with the exclusion of moisture. The conversion of the acetylenic carbinol used amounts to 12.1 g. corresponding to 65.7% by weight. The yield of 7-methoxy-3,7-dimethyl-oct-2-en-1-al amounts to 10.2 g. corresponding to 84.3% by weight.

EXAMPLE 14

12.4 g. of 1-ethynyl-1-cyclohexanol, 2 g. tris-[tri-($\alpha,\alpha,\alpha$-trifluoro-m-tolyl)-siloxy]-vanadium oxide and 100 ml of high-boiling paraffin oil are heated to 105°C. for 5 hours with the exclusion of moisture. The conversion of the acetylenic carbinol used amounts to 9.5 g. corresponding to 76.6% by weight.

Two isomeric products, namely cyclohexylidene-acetaldehyde (I) and cyclohex-1-en-1-yl-acetaldehyde (II) are isolated in this isomerisation. The total yield of I and II based on the reacted starting material amounts to 7.9 g. corresponding to 83.0% by weight and the molar ratio of the two aldehydes I and II to one another is 38.4:61.6.

EXAMPLE 15

13.2 g of 3-hydroxy-3-phenyl-prop-1-yne, 2 g. tris-[tri-($\alpha,\alpha,\alpha$-trifluoro-m-tolyl)-siloxy]-vanadium oxide and 100 ml of silicon oil are heated to 110°C for 4 hours with the exclusion of moisture. The conversion of the acetylenic carbinol used amounts to 10.9 g corresponding to 82.6% by weight. The yield of cinnamaldehyde amounts to 10.5 g corresponding to 96% by weight.

EXAMPLE 16

12.6 g of 2-hydroxy-2-methyl-hept-3-yne, 0.7 g tris-[tri-($\alpha,\alpha,\alpha$-trifluoro-m-tolyl)-siloxy]-vanadium oxide and 150 ml of high-boiling paraffin oil are heated at 100°C for 6 hours with the exclusion of moisture. The conversion of the acetylenic carbinol used amounts to 11.0 g corresponding to 87.2% by weight. The yield of 2-methyl-hept-2-en-4-one amounts to 10.55 g corresponding to 96.0% by weight.

EXAMPLE 17

10 g of 4-ethynyl-4-hydroxy-1,-1-ethylenedioxy-3,5,5-trimethylcyclohex-2-ene, 0.15 g of hydroquinone, 0.02 ml of tris-[tri-($\alpha,\alpha,\alpha$-tri-fluoro-p-tolyl)-siloxy]-vanadium oxide and 100 ml of dry toluene are heated to boiling at 110°C for 9 hours with the exclusion of moisture. The solvent is subsequently distilled off under reduced pressure at 40°C. The residual isomer mixture of cis/trans (4,4-ethylenedioxy-2,6,6-trimethyl-cyclohex-2-en-1-ylidene)-acetaldehyde boils in a high vacuum at 110°–125°C/0.1 mm Hg after rectification. The conversion of the acetylenic carbinol used amounts to 7.5 g corresponding to 75% by weight. The aldehyde is obtained in a yield of 6.95 g corresponding to 92.5% by weight.

EXAMPLE 18

800 ml of liquid ammonia are placed in a 2 liter three-necked flask fitted with a mechanical stirrer, dropping funnel and Claisen head having a dry-ice condenser. 10 g of lithium are then introduced within 30 minutes while stirring. The mixture is then stirred for 60 minutes. Acetylene is subsequently passed through the deep-blue solution until the solution becomes almost colorless. The dry-ice condenser is removed and replaced by a tube filled with potassium hydroxide. The ammonia is evaporated and replaced by the same amount of diethyl ether. The resulting suspension of lithium acetylide is treated at room temperature with 30 minutes with a solution of 20 g of 1,1-ethylenedioxy-3,5,5-trimethyl-cyclohex-2-en-4-one in 100 ml of diethyl ether. The mixture is stirred for 18 hours and then carefully poured on to a mixture of ice and 400 ml of a 25% by weight aqueous ammonium chloride solution. The diethyl ether phase is separated, washed with water, dried over sodium sulphate, filtered and evaporated under reduced pressure. The residual crystalline 4-ethynyl-4-hydroxy-1,1-ethylenedioxy-3,5,5-trimethyl-cyclohex-2-ene melts at 85°–86°C after recrystallization from ethyl acetate/petroleum ether.

I claim:
1. Compounds of the general formula

 (III)

wherein $R_6$ is phenyl substituted, in one or more positions with an electron withdrawing group; R is selected from the group consisting of alkyl, cycloalkyl, lower alkyl substituted cycloalkyl, phenyl, phenyl lower alkyl, lower alkyl substituted phenyl; lower alkyl substituted phenyl lower alkyl, —Si $(R_6)_3$ and Si $(R_5)_3$; $R_5$ is selected from the group consisting of alkyl, phenyl lower alkyl, cycloalkyl, lower alkyl-substituted cycloalkyl, phenyl; lower alkyl-substituted phenyl-lower alkyl, and lower alkyl substituted phenyl; $m$ is an integer from 1 to 3; and $n$ is an integer of from 0 to 2 with the proviso that the sum of $m$ and $n$ is 3.

2. The compound of claim 1, wherein said electron withdrawing group is a halogen.

3. The compound of claim 2, wherein said compound is tris-[tri-(p-chlorophenyl)-siloxy]-vanadium oxide.

4. The compound of claim 2, wherein said compound is tris-[tri-(p-fluorophenyl)-siloxy]-vanadium oxide.

5. The compound of claim 2, wherein said compound is tris-[tri-(p-bromophenyl)-siloxy]-vanadium oxide.

6. The compound of claim 2, wherein said compound is tris-[tri-($\alpha,\alpha,\alpha$-trifluoro-m-tolyl)-siloxy]-vanadium oxide.

7. The compound of claim 2, wherein said compound is tris-[tri-($\alpha,\alpha,\alpha$-trifluoro-p-tolyl)-siloxy]-vanadium oxide.

8. The compound of claim 1, wherein said compound is tris-[bis-(3-nitro-4-bromophenyl)-(4-bromophenyl)-siloxy]-vanadium oxide.

9. The compound of claim 1, wherein said compound is tris-[tri-(4-biphenylyl)-siloxy]-vanadium oxide.

10. The compound of claim 1, wherein said compound is (tri-p-fluorophenyl)-siloxy-bis-(triphenyl-siloxy)-vanadium oxide.

11. The compound of claim 2, where said compound is bis-[tri-(p-fluorophenyl)-siloxy]-triphenyl-siloxy-vanadium oxide.

12. The compound of claim 2, wherein said compound is bis-[tri-(p-bromophenyl)-siloxy]-cyclohexyloxy-vanadium oxide.

* * * * *